US009760686B2

(12) United States Patent
Garnavi et al.

(10) Patent No.: US 9,760,686 B2
(45) Date of Patent: Sep. 12, 2017

(54) BALANCED ULTRAVIOLET LIGHT EXPOSURE RECOMMENDATIONS

(71) Applicant: International Business Machines Corporation, Armonk, NY (US)

(72) Inventors: Rahil Garnavi, Melbourne (AU); Timothy M. Lynar, Kew (AU); Suraj Pandey, Parkville (AU); John M. Wagner, Carlton (AU); Ziyuan Wang, Malvern East Victoria (AU)

(73) Assignee: International Business Machines Corporation, Armonk, NY (US)

( * ) Notice: Subject to any disclaimer, the term of this patent is extended or adjusted under 35 U.S.C. 154(b) by 503 days.

(21) Appl. No.: 14/249,692

(22) Filed: Apr. 10, 2014

(65) Prior Publication Data
US 2015/0294080 A1  Oct. 15, 2015

(51) Int. Cl.
  *G06F 19/00*  (2011.01)
(52) U.S. Cl.
  CPC .................... *G06F 19/3431* (2013.01)
(58) Field of Classification Search
  CPC .................... G06Q 40/08; G06Q 10/10
  See application file for complete search history.

(56) References Cited

U.S. PATENT DOCUMENTS

| | | | |
|---|---|---|---|
| 4,882,598 A | 11/1989 | Wulf | |
| 5,306,917 A | 4/1994 | Black et al. | |
| 6,348,694 B1 | 2/2002 | Gershteyn et al. | |
| 6,936,824 B2 | 8/2005 | Takada | |
| 7,271,393 B2 | 9/2007 | Makela et al. | |
| 7,544,949 B2 | 6/2009 | Hwang | |
| 8,044,363 B2 | 10/2011 | Ales et al. | |
| 8,503,791 B2 * | 8/2013 | Conwell | ........... G06F 17/30265 382/190 |

(Continued)

FOREIGN PATENT DOCUMENTS

| | | |
|---|---|---|
| JP | 2006071581 A | 3/2006 |
| RU | 2317016 | 2/2008 |

(Continued)

OTHER PUBLICATIONS

Lizette Borreli, "Drinking Alcohol in the Sun May Increase Skin Cancer Risk: Chemicals in Cocktails Cause Skin Sensitivity and Cell Damage", Medical Daily, medicaldaily.com, Jan. 29, 2014 available at http://www.medicaldaily.com/drinking-alcohol-sun-may-increase-skin-cancer-risk-chemicals-cocktails-cause-skin-268209.*

(Continued)

*Primary Examiner* — Victoria P Shumate
*Assistant Examiner* — Gregory Moseley
(74) *Attorney, Agent, or Firm* — Fleit Gibbons Gutman Bongini Bianco PL; Jon Gibbons

(57) ABSTRACT

Ultraviolet light poses both health benefits and health risks. A method, device and computer storage program balances the health risks and benefits of ultraviolet light exposure with personal sensitivities and preferences for these health risks and benefits. An ultraviolet light exposure level of a subject person is estimated by monitoring data from a plurality of sources. A personal sensitivity to ultraviolet light exposure is also estimated from data from various sources. A recommendation for the subject person is generated based upon the estimated risks and benefits of ultraviolet light exposure.

18 Claims, 5 Drawing Sheets

(56) References Cited

U.S. PATENT DOCUMENTS

| | | | |
|---|---|---|---|
| 2003/0175721 A1 | 9/2003 | Box et al. | |
| 2006/0251338 A1* | 11/2006 | Gokturk | G06F 17/30253 382/305 |
| 2007/0064989 A1* | 3/2007 | Chhibber | A61B 5/442 382/128 |
| 2009/0224168 A1 | 9/2009 | Santibanez-Viani et al. | |
| 2009/0248445 A1* | 10/2009 | Harnick | G06F 19/322 705/3 |
| 2010/0185064 A1* | 7/2010 | Bandic | A61B 5/0059 600/306 |
| 2011/0191272 A1* | 8/2011 | McGuire | G06N 5/00 706/11 |
| 2012/0122698 A1 | 5/2012 | Stacey et al. | |
| 2012/0326046 A1* | 12/2012 | Aslam | G01J 1/0233 250/372 |
| 2012/0326873 A1* | 12/2012 | Utter, II | G06F 3/016 340/573.1 |
| 2013/0077833 A1* | 3/2013 | Kritt | G06K 9/00677 382/118 |
| 2013/0325399 A1* | 12/2013 | Yuen | A61B 5/0002 702/178 |
| 2014/0088991 A1* | 3/2014 | Bakes | G06F 19/3418 705/2 |
| 2015/0131872 A1* | 5/2015 | Ganong | G06K 9/00677 382/118 |
| 2016/0224671 A1* | 8/2016 | Jung | G06F 17/30091 |

FOREIGN PATENT DOCUMENTS

| | | |
|---|---|---|
| RU | 2331878 | 8/2008 |
| WO | 2005002437 | 1/2005 |

OTHER PUBLICATIONS

Richard L. McKenzie, J. Ben Liley and Lars Olof Bjorn, "UV Radiation: Balancing Risks and Benefits", Photochemistry and Photobiology, Jan. 2009, 88-98.*

MedicineNet.com, "Sun-Sensitive Drugs (Photosensitivity to Drugs)", http://www.medicinenet.com/sun-sensitive_drugs_photosensitivity_to_drugs/article.htm Jul. 18, 2012.

* cited by examiner

BALANCED ULTRAVIOLET LIGHT EXPOSURE RECOMMENDATIONS

BACKGROUND

This disclosure broadly relates to the field of estimating levels of exposure of an individual to ultraviolet light, and more particularly to a recommendation generating apparatus and process.

Skin cancer is a cancer that forms in the tissues of the skin when skin cells are damaged, including by overexposure to ultraviolet light from the sun. There are three main types of skin cancer, named after the type of skin cell from which they arise: melanoma, which forms in melanocytes, the skin cells that make pigment; basal cell carcinoma, which forms in the lower part of the epidermis, the outer layer of the skin; and squamous cell carcinoma, which forms in squamous cells, the flat cells that form the surface of the skin. Of these three, melanoma is the least common skin cancer, but also is the most aggressive, the most likely to spread and, if left untreated, fatal. Sun exposure is a significant risk factor for all three types of skin cancer. There are many other risk factors, including personal and family histories; skin and hair colour; and even eye colour. Other risk factors include moles and immune system strength.

Skin cancer is the most common of all cancers, accounting for nearly half of all cancers in the United States; more than 3.5 million skin cancers are diagnosed annually in more than 2 million people, with melanoma accounting for more than 75,000 cases and over 8,500 deaths. About one in five Americans will develop skin cancer in their lifetime, and about one in 50 Americans will develop melanoma in their lifetime. Skin cancer is also not limited to the elderly: melanoma is the most common form of cancer for young adults 25-29 years old and the second most common form of cancer for adolescents and young adults 15-29 years old. One person dies of melanoma every 57 minutes. Skin cancer also accounts for many billions of dollars in both direct and indirect spending. In the United States, according to the National Cancer Institute, the total direct costs associated with the treatment for non-melanoma skin cancer in 2004 was $1.5 billion, and the estimated total direct cost associated with the treatment of melanoma in 2010 was $2.36 billion.

Exposure to ultraviolet light from the sun can not only result in skin cancer but also can result in changes in skin characteristics such as skin colour or tan, freckling, and skin blemishes. Such changes are often recorded in images that may be stored on social media databases or web sites. Such databases are able to accumulate numerous images over an extended period of time. Analysis of an ultraviolet light exposure profile may be beneficial in mitigating harm caused by exposure to ultraviolet light exposure.

SUMMARY

A method, device and computer storage program balances the health risks and benefits of ultraviolet light exposure with personal tolerances and preferences for these health risks and benefits.

A method in a computer coupled to a network, the method comprises estimating an ultraviolet light exposure level of a subject person based upon data received from a plurality of sources coupled to the network; estimating a personal sensitivity to ultraviolet light of the subject person based upon personal attributes of the subject person received from at least one database coupled to the computer; assessing a health risk of the subject person due to ultraviolet light exposure based upon the ultraviolet light exposure level of the subject person and the personal sensitivity to ultraviolet light of the subject person; assessing a health benefit of the subject person due to ultraviolet light exposure based upon the ultraviolet light exposure level of the subject person and the personal sensitivity to ultraviolet light of the subject person; generating a balanced ultraviolet light exposure recommendation for the subject person based upon the health risk and the health benefit; and rendering the recommendation on an output device coupled to the computer.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

Figure 1:
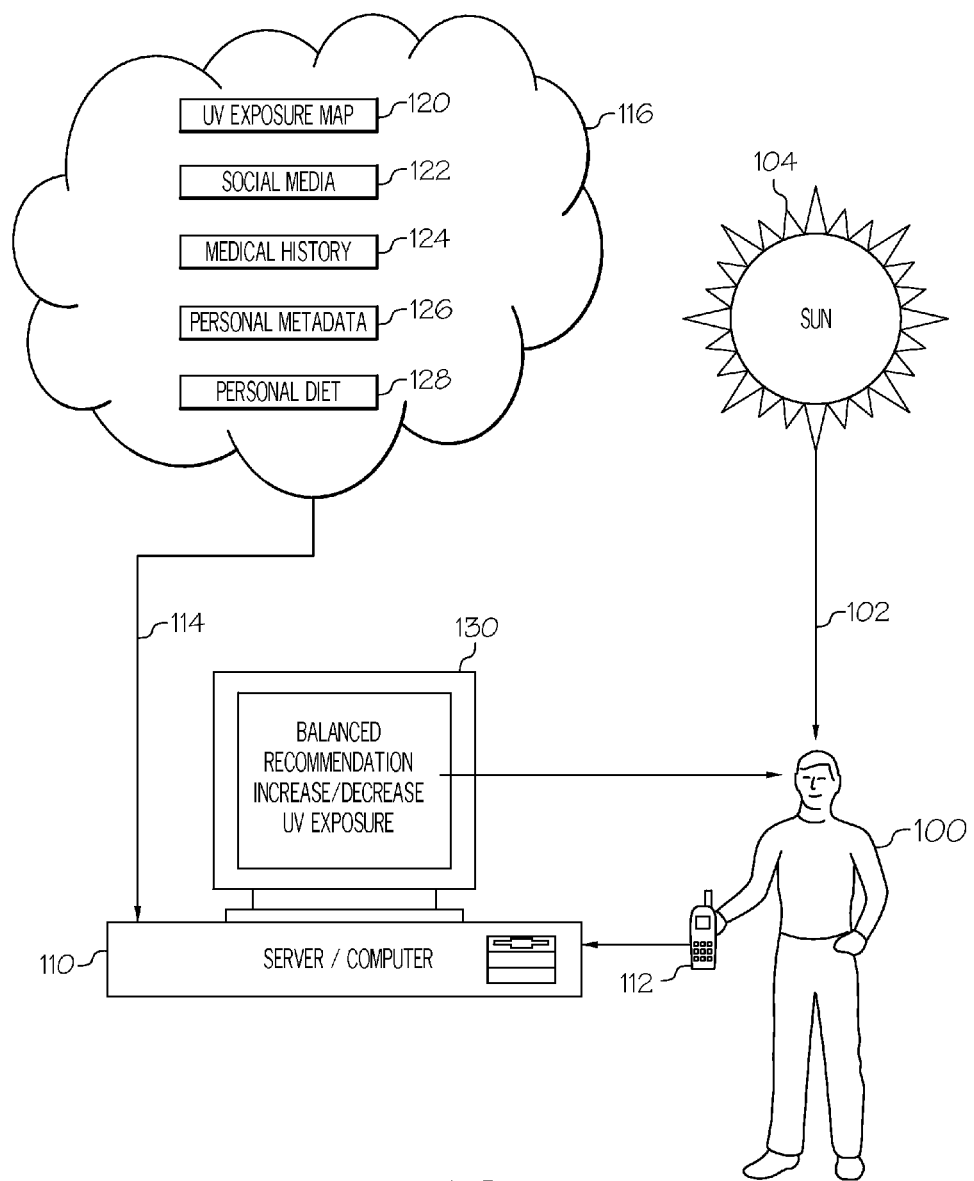
FIG. 1 illustrates an example context of an environment for generating a balanced ultraviolet light exposure recommendation for a subject person.

In the following discussion, details are provided to help thoroughly understand the present disclosure. However, it is apparent to those of ordinary skill in the art that even though there may be no such details, the understanding of the present disclosure would not be influenced. In addition, it should be further appreciated that any specific terms or applications used herein are only for the convenience of description, and thus the present disclosure should not be limited to only use in any specific terms or applications represented and/or implied by such terms.

Generally speaking, ultraviolet light, UVB (medium wavelength of approximately 315-280 nm) in particular, from sun exposure is the major cause of skin cancer and other skin diseases. Risk factors for melanoma skin cancer and other diseases include ultraviolet light exposure from sunshine or tanning beds, moles, fair skin, freckling, light hair, a family history of melanoma, immune suppression, age, gender, xeroderma pigmentosum, history of indoor tanning, and blue or green eyes. Protection from burning in the sun is vital. People with lots of moles, red hair, fair skin and a family history of such diseases should take care as they are more at risk. Family history may be an indicator of an increased risk of melanoma, such indicators include one or more genetically related members having had melanoma, more than one melanoma, or both melanoma and pancreatic cancer. Such indicators may be indicative of a gene mutation that increases the risk of melanoma. Of course being diagnosed with melanoma is also indicative of the increased risk. The use of sunscreen is effective and recommended to prevent both melanoma and squamous cell carcinoma. While a relationship exists between family history, diet, personal complexion and sun exposure, a key is to achieve the right balance between the amount of time spent in the sun or being exposed to ultraviolet light and the levels of vitamin D needed for good health. The sun is a viable source for vitamin D and individuals may have a variable personal sensitivity to ultraviolet light. Personal sensitivity to ultraviolet light includes erythema, the reddening of the skin, or persistent pigment darkening and may also include a personal tolerance to or susceptibility to risk associated with exposure to ultraviolet light. The inventors have discovered that it is important to balance the amount of ultraviolet violet radiation received by a subject person. The balancing includes an automated process for assessing the health risk and the health benefit of ultraviolet light for the subject person based upon a number of factors and providing a recommendation.

In one example of an automated process for balancing the risks and benefits ultraviolet light exposure, the ultraviolet light exposure of a subject person is continuously monitored. Photos of the subject person and the status posted on one or more social networks are continuously monitored. Photos and activities of the subject person so posted can be indicative of ultraviolet light exposure. For examples outdoor photos in the sunlight are indicative of the subject person receiving ultraviolet light, and the skin color or changes in skin color may be indicative of long term exposure to ultraviolet light. Also, statements of activities such as surfing may be indicative of exposure to ultraviolet light while activities such as bowling may have a contrary indication. The monitoring may also include wearable electronic devices which may include sensors able to estimate an amount exposure to ultraviolet light. Such devices include cameras, cellphones, laptops, tablets, PDAs and other such devices. The wearable electronic device may also include location determining abilities such as GPS to determine a location and time of the location of the subject person. That time and location may then be compared with an ultraviolet exposure map to estimate the ultraviolet light exposure of the subject person. Information from a wearable electronic device may be communicated through a cellular network or other wired or wireless network for processing by the automated process. The continuously monitored ultraviolet light exposure data may be integrated with historic exposure data to provide long term analysis for the balancing of the risks and benefits of ultraviolet light exposure. Furthermore, personal sensitivity influencing factors may be included in the analysis. Such personal sensitivity factors include moles, fair skin, freckling, light hair, a family history of melanoma, immune suppression, age, gender, xeroderma pigmentosum, history of indoor tanning, blue or green eyes, diet including foods like carrots which may increase personal sensitivity to ultraviolet light, medications including photosensitive medications which may decrease personal sensitivity to ultraviolet light, needed level of vitamin D, sunscreen use, mental state, emotional state, baldness, intake of vitamin D or foods such as certain types of fish providing vitamin D, intake of alcohol and other factors. Using the analysis, continuous feedback and reporting of personal history and risk are provided.

The process includes a method for collecting data and integrating the data with historical data related to the subject person. Ultraviolet light exposure is collected from various location services, photographs and videos of the subject person uploaded to social media databases (using facial recognition or other metadata) and other information from wearable devices. Based there upon, an ultraviolet exposure map may be used based upon location information. The ultraviolet light exposure of the subject person is then calculated in response thereto. Changes in skin color and blemishes recorded over time are analyzed and changes are recorded. Based thereupon, the exposure to ultraviolet light of the subject person may be assessed. The assessment may be calibrated based upon observed meteorological data, personal data, image data, personal metadata and peer data. Alerts and reports may be generated based upon the assessment. The process may then continuously calibrate the ultraviolet exposure reading with the latest data collected and update reports may be generated based upon the assessment. The reports and recommendations may be rendered upon a display or printer 130 for use by the subject person or a doctor or other associate of the subject person.

An analysis of the relationship and impact of the aforementioned factors to a risk model can be created through at least one or more techniques. For example, applying rule based heuristics, machine based learning techniques may be used to learn the behavior of the subject person over time. Seasonal behaviors may be determined such as yearly activities like an annual snow ski trip, holiday travels may be determined, and daily or other periodic routines determined such as a daily bike ride to work or a weekend trip to the beach. Ultraviolet light exposures may be associated with such behaviors.

In an example of an enhancement, crowd sourced contextual information may be incorporated. Also, geographic location may be enhanced and include location information from location tags included in social media posts, and demographic data on skin related diseases applied to the analysis. Also, skin related features may be extracted from images provided by the subject person using image processing techniques.

FIG. 1 illustrates an example context of an environment for generating a balanced ultraviolet light exposure recommendation for a subject person. Subject person 100 is shown as being exposed to ultraviolet light 102 from an object such as the sun 104. The ultraviolet light exposure may be from any other object able to generate ultraviolet light and expose the subject person to the ultraviolet light. Such objects include tanning booths, electronic welding equipment and ultraviolet disinfection equipment. A computer or server 110 receives data from a number of sources including a cellphone or other wearable device 112 or other remote databases coupled to the computer or server through a network 114. The computer or server may operate using a computer storage program product comprising a storage medium readable by a processing circuit and storing instructions for execution by the processing circuit configured to perform a method of the present invention. The wearable device may include a cellphone, tablet, personal computer or camera and may be able to estimate an exposure level of ultraviolet light using a camera or other sensor and may be able to determine the time and location of the subject person using GPS or other location determining system.

The network 114 may include the Internet. The remote databases may include in one or more clouds 116 or databases coupled to the network. In other examples, one or more of the databases may be included in an intranet or other local area network or may be included in the computer or server itself. The databases may include an ultraviolet exposure map 120 that when combined with the time and location of the subject person may be used to estimate ultraviolet light exposure. The ultraviolet exposure map may be based upon weather or other meteorological databases wherein the time, location and intensity of ultraviolet light may be estimated based upon time, sun position, cloud coverage, temperature, precipitation, pollution and other atmospheric conditions. Social media database(s) 122 may be mined for photographs of the subject person or other data such as calendar data, activities, emails, texts, tweets, or postings that may provide a basis for estimating ultraviolet exposure of the subject person. A medical history database 124 may provide indications of the personal sensitivity of the subject person by including a history of skin diseases of the subject person or persons genetically related to the subject person. The medical database may further include a history of an intake of photosensitive medications by the subject person. A personal metadata database 126 may include factors such as ages, ethnicity, mental state, emotional state or even baldness of the subject person. These factors may be useful in estimating personal sensitivity to ultraviolet light of the subject person. Personal diet database 128 may include indications of the food intake of the subject person that may affect the subject person's personal sensitivity to ultraviolet light, such food intakes including alcohol, vitamin D vitamins or foods including vitamin D, carrots or other foods having an impact on the personal sensitivity of the subject person to ultraviolet light.

The server or computer 110 may be any kind of computing device. It may be a personal computer at a home or an office of the subject person, it may be a computing process operating remotely on a server or other cloud based software service, or it may be a process operating on a cellphone, tablet or other wearable device of the subject person. The process operating upon the server or computer 110 estimates the personal sensitivity to ultraviolet light of the subject person, estimates the ultraviolet light exposure of the subject person, assesses the health risk and the health benefit of ultraviolet light exposure, provides an ultraviolet light exposure recommendation including to either increase or decrease, or not to change the current ultraviolet light exposure behavior of the subject person. The recommendation may be rendered on a display or printer for use by the subject person.

Figure 2:
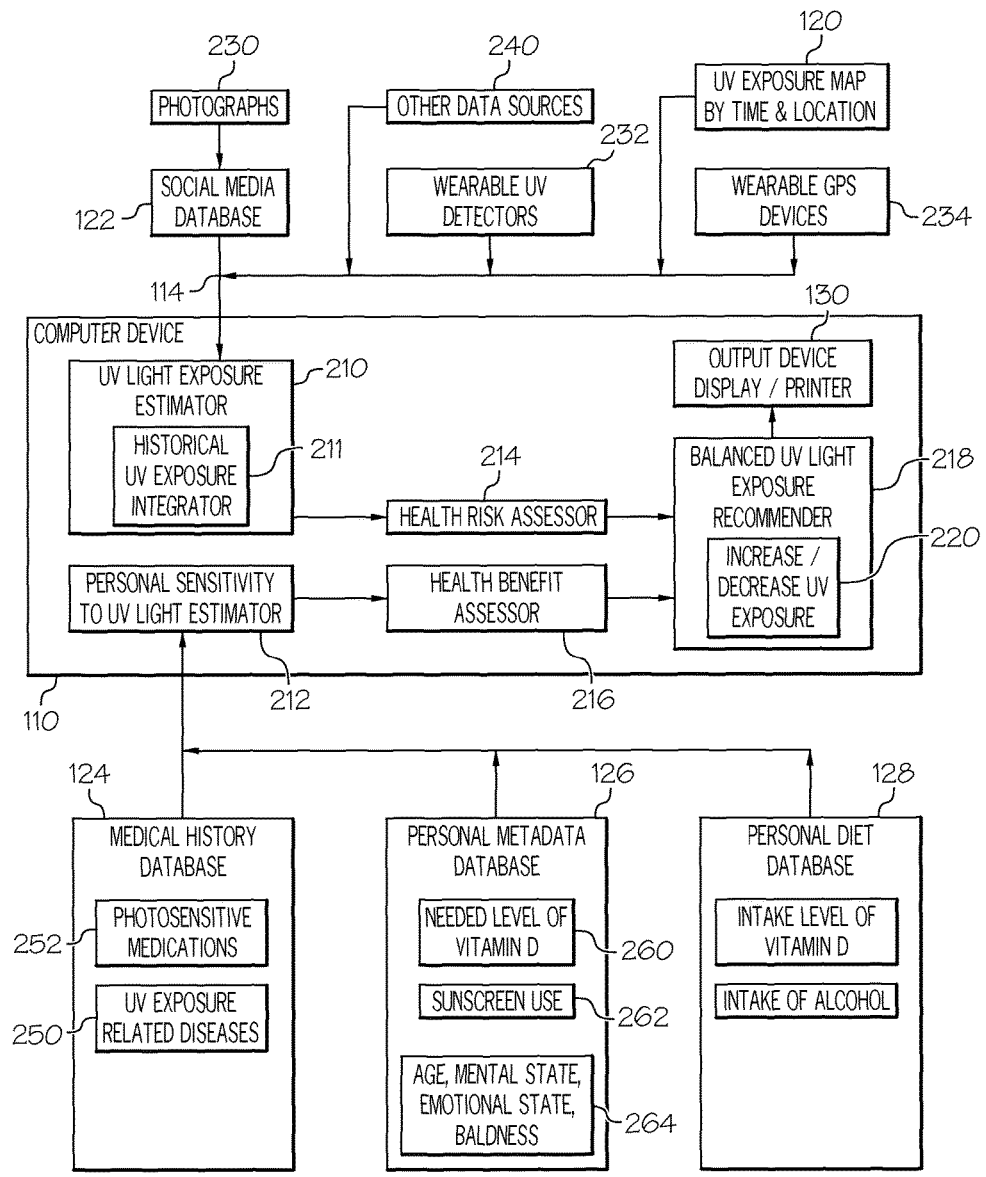
FIG. 2 illustrates an example block diagram of a system for generating a balanced ultraviolet light exposure recommendation for a subject person.

FIG. 2 illustrates an example block diagram of a system for generating a balanced ultraviolet light exposure recommendation for a subject person. A computer device 110 coupled to a network 114. The computer device comprises an ultraviolet light exposure estimator 210 adapted to estimate an ultraviolet light exposure level of a subject person based upon data received from a plurality of sources coupled to the network. The computer device also comprises a personal sensitivity to ultraviolet light estimator 212 adapted to estimate a personal sensitivity to ultraviolet light of the subject person based upon personal attributes of the subject person received from at least one database coupled to the computer, and includes a historical ultraviolet light exposure integrator for estimating long term exposure characteristics of the subject person. The computer device also includes a health risk assessor 214 adapted to assess a health risk of the subject person due to ultraviolet light exposure based upon the ultraviolet light exposure level of the subject person and the personal sensitivity to ultraviolet light of the subject person. The computer device also includes a health benefit assessor 216 adapted to assess a health benefit of the subject person due to ultraviolet light exposure based upon the ultraviolet light exposure level of the subject person and the benefits of ultraviolet light exposure of the subject person. Such health benefits include conversion of ultraviolet light to vitamin D as well as the cosmetic advantages of a tanned skin tone. An initial exposure to ultraviolet light may provide the benefit of increasing vitamin D, while exposure beyond an initial threshold may provide a marginal vitamin D benefit increasing a health risk of diseases resulting from exposure to ultraviolet light. The threshold at which ultraviolet exposure transitions from a health benefit to a health risk varies from person to person based on a number of factors including factors mentioned herein. In one example, a darker skin complexion may require greater ultraviolet light exposure to increase vitamin D levels, while a lighter skin complexion may have an increased health risk to exposure to ultraviolet light. A balanced ultraviolet light exposure recommender 218 is adapted to generate a balanced ultraviolet light exposure recommendation for the subject person based upon the health risk and the health benefit including recommending an increased exposure to ultraviolet light 220 based upon the health benefit exceeding the health risk, recommending a decreased exposure to ultraviolet light based upon the health risk exceeding the health benefit, and recommending maintenance of a current level of ultraviolet exposure. An output device 130 is adapted to render the recommendation on a display or printed paper and may include a display or a printer or both.

Social media database 122 includes photographs or video images 230 of the subject person which may be used as previously described by the ultraviolet light exposure estimator to estimate an amount of exposure of the subject person to ultraviolet light. Wearable ultraviolet detectors 232 may include cellphone 112 and have detectors such as ultraviolet sensitive cameras to estimate an amount of exposure of the subject person to ultraviolet light. An ultraviolet detector may be a standalone wearable device or may be incorporated into any of a number of devices such as the cellphone, a tablet, laptop or a camera. Wearable GPS device 234 determines the time and location of the subject person and may be a standalone wearable device or may be incorporated into any of a number of devices such as the cellphone, a tablet, laptop or camera. When the time and location of the subject person are combined with data from the ultraviolet exposure map 120, an amount of exposure of the subject person to ultraviolet light may be estimated. While the example shows several database sources for estimating an amount exposure to ultraviolet light, it should be appreciated that other data sources 240 may also be used while remaining within the scope of the description. Thus, information from a plurality of sources coupled to the computer device through a network is used to estimate the ultraviolet light exposure level of the subject person.

The personal sensitivity to ultraviolet light estimator 212 receives data on personal attributes of the subject person from various databases coupled to the computer device. The medical history database 124 includes information on ultraviolet light exposure related diseases 250 of either the subject person or of persons genetically related to the subject person. Such diseases can include skin cancers such as melanoma, basal cell carcinoma, and squamous cell carcinoma and may be linked to a medical database used by physicians of the subject person. Additionally, the medical history database may include information regarding the intake of photosensitive medications include medications that suppress photoprotectant characteristics of melanin. The risk of sunburn can be increased by pharmaceutical products that sensitize users to ultraviolet radiation. Photosensitive medications may increase or decrease the personal sensitivity to ultraviolet light and may include certain antibiotics, antihistamines, malaria medications, cancer and cardiac drugs, oral contraceptives, tranquilizers, skin and acne medications and psychiatric drugs. The personal metadata database may include sunscreen use and a needed level of vitamin D 260 (which may alternately be included in the medical history database). For example, sunscreen use may be estimated by entries by the subject person, by monitoring sunscreen purchases by the subject person or by mining a database such as a social media database for comments or images indicative of the use of sunscreen by the subject person. The personal metadata database may also include information such as age, mental state, emotional state, baldness and family history. Mental and emotional state may also be estimated by mining social media database or other communications such as emails, texts, or tweets for language or images indicative of the mental or emotional state of the subject person. Personal diet database 128 may include information regarding the intake of vitamin D or alcohol which may be estimated in any of the aforementioned approaches. The information in the databases as well as other databases allow the personal sensitivity of the subject person to ultraviolet light to be estimated.

In one example of the device, the personal sensitivity to ultraviolet light estimator 212 estimates an amount of vitamin D corresponding to a good health of the subject person and a level of vitamin D intake associated with the subject person. The health benefit assessor 216 estimates the level of vitamin D intake to be less than the amount of vitamin D corresponding to the good health, and the balanced ultraviolet light exposure recommender 218 recommends an increased exposure to ultraviolet light based upon the level of vitamin D intake being less than the amount of vitamin D corresponding to the good health. In this example, if the person has a constant requirement for vitamin D. The actual amount of vitamin D received by the subject person may be provided through ultraviolet light exposure as well as intake of food or vitamin D supplements. If the actual amount of vitamin D received is less than the requirement of vitamin D as estimated by the monitoring of the various databases, then the recommendation to increase exposure to ultraviolet light is generated. If the recommendation is not followed, then a subsequent recommendation may be a stronger recommendation to increase exposure to ultraviolet light. The subsequent recommendation may occur within a set time frame or based on a number of analyzed variables. If the vitamin D deficiency progresses from severe to critical, a warning alarm may be generated.

In another example, the health risk assessor 214 estimates the ultraviolet light exposure level to exceed the personal sensitivity, and the balanced ultraviolet light exposure recommender 218 recommends a decreased exposure to ultraviolet light based upon the ultraviolet light exposure level being greater than the personal sensitivity.

In another example, one of the plurality of sources includes a wearable location detection device 234 worn by the subject person adapted to determine a time and location of the subject person and the ultraviolet light exposure estimator 210 receives an ultraviolet light exposure map 120 and estimates the ultraviolet light exposure level based upon the time and location of the subject person and the ultraviolet light exposure map.

Figure 3:
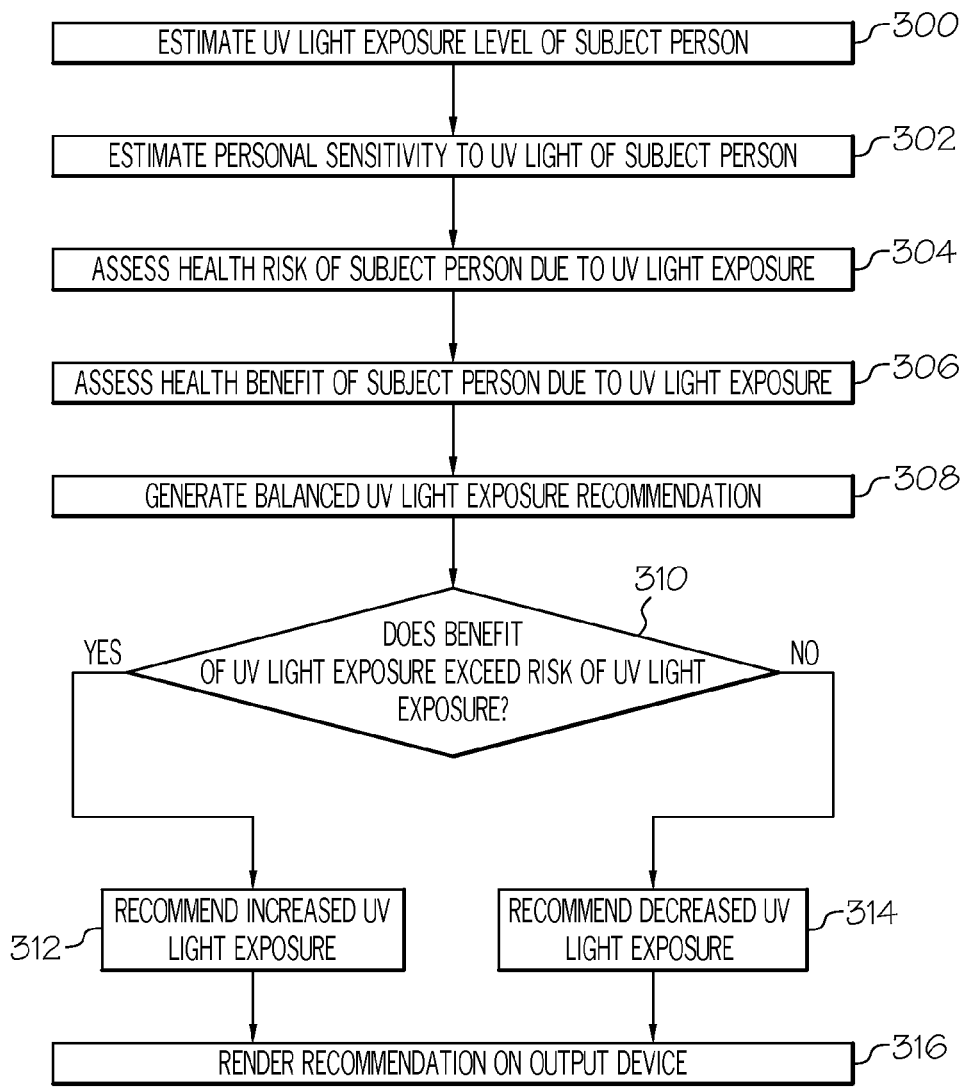
FIG. 3 illustrates an example flow diagram of a process for generating a balanced ultraviolet light exposure recommendation for a subject person.

FIG. 3 illustrates an example flow diagram of a process for generating a balanced ultraviolet light exposure recommendation for a subject person. In a computer coupled to a network, the method of the flow diagram includes estimating an ultraviolet light exposure level of a subject person based upon data received from a plurality of sources coupled to the network. Step 302 estimates a personal sensitivity to ultraviolet light of the subject person based upon personal attributes of the subject person received from at least one database coupled to the computer. Step 304 assesses a health risk of the subject person due to ultraviolet light exposure based upon the ultraviolet light exposure level of the subject person and the personal sensitivity to ultraviolet light of the subject person. Step 306 assesses a health benefit of the subject person due to ultraviolet light exposure based upon the ultraviolet light exposure level of the subject person and the personal sensitivity to ultraviolet light of the subject person. Step 308 generates a balanced ultraviolet light exposure recommendation for the subject person based upon the health risk and the health benefit. The recommendation in this example is estimated by analyzing the heath benefit and the health risk of ultraviolet light exposure. The process recommends an increased exposure to ultraviolet light based upon the health benefit exceeding the health risk at step 312, and recommends a decreased exposure to ultraviolet light based upon the health risk exceeding the health benefit at step 314. In another example the recommendation may be to maintain a current level of ultraviolet light exposure if the benefits and risks are balanced. Then step 316 renders the recommendation on an output device coupled to the computer.

Figure 4:
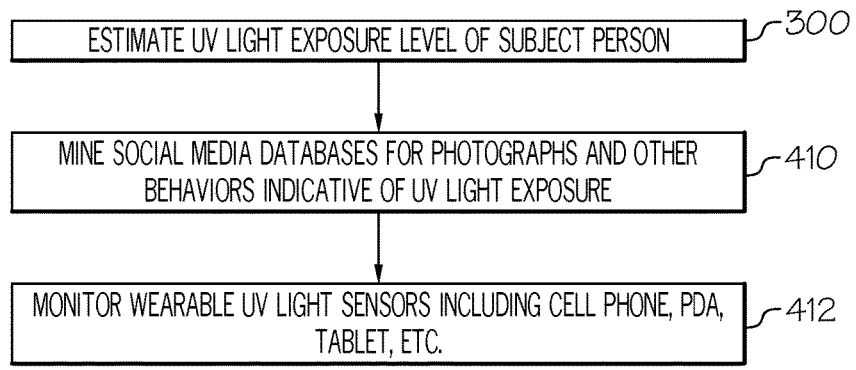
FIG. 4 illustrates an example of a more detailed process for estimating the ultraviolet light exposure level of the subject person.

FIG. 4 illustrates an example of a more detailed process for estimating the ultraviolet light exposure level of the subject person. The estimation of ultraviolet light exposure level of the subject person 300 includes mining social media for photographs of the subject person recorded by at least one of the plurality of sources or other behaviors indicative of ultraviolet light exposure 410. Then the ultraviolet light exposure level based is estimated upon a skin color of the subject person within the photographs or other behavioral determination. Step 412 checks for a wearable ultraviolet light sensor worn by the subject person and then the ultraviolet light exposure level of the subject person includes monitoring the wearable ultraviolet sensor.

Figure 5:
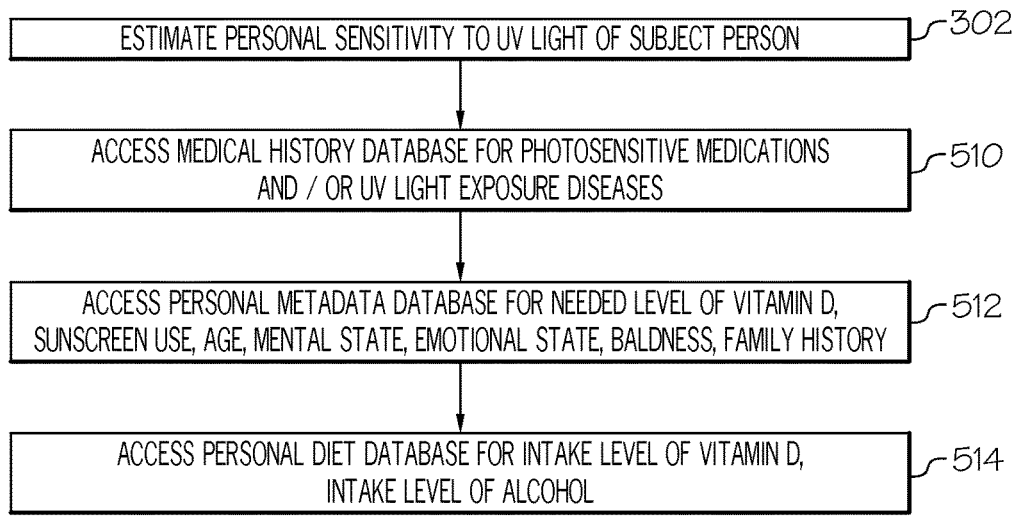
FIG. 5 illustrates an example of a more detailed process for estimating the personal sensitivity to ultraviolet light of the subject person.

FIG. 5 illustrates an example of a more detailed process for estimating the personal sensitivity to ultraviolet of the subject person. In step 510 the medical history database is accessed for photosensitive medications and/or ultraviolet light exposure diseases. The personal metadata database is accessed for needed levels of vitamin D, sunscreen use, age, mental state, emotional state, baldness and family history at step 512. And step 514 accesses the personal diet database for intake level of vitamin D and intake level of alcohol, as well as the intake of other items that may affect personal sensitivity.

Figure 6:
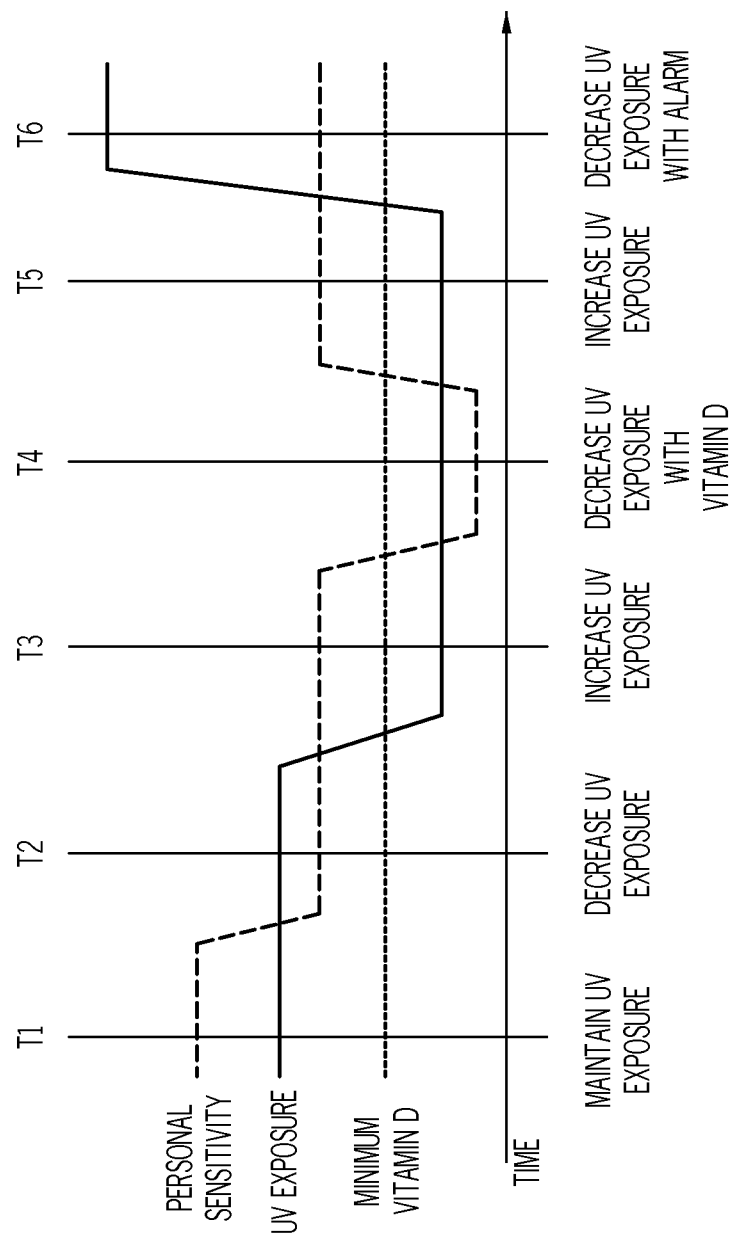
FIG. 6 illustrates an example of generating a balanced ultraviolet light exposure recommendation for a subject person.

FIG. 6 illustrates an example of generating a balanced ultraviolet light exposure recommendation for a subject person. The graph of FIG. 6 shows the personal sensitivity, ultraviolet light exposure and minimum level of vitamin D of the subject person over time verses generated recommendations. At T1, the personal sensitivity exceeds the ultraviolet exposure, thereby providing a low health risk, and the ultraviolet exposure exceeds the minimum level of vitamin D, thereby providing a low health benefit. In response, the recommendation generated is to maintain the current level of ultraviolet light exposure. At T2, the personal sensitivity has been decreased, perhaps for example because a relative of the subject person had been diagnosed with a skin disease or the subject person had stopped using sunscreen. At T2, the ultraviolet exposure exceeds the minimum level of vitamin D, thereby providing a low health benefit, and the ultraviolet exposure exceeds the personal sensitivity, thereby providing a high health risk. In response, the recommendation generated is to decrease ultraviolet exposure. At time T3, the ultraviolet exposure is decreased. The decrease may be for example, in response to the recommendation of T2 or based upon a seasonal change in sunlight exposure such as a change from autumn to winter, or other factors decreasing ultraviolet light exposure. At T3 the personal sensitivity exceeds the ultraviolet exposure, thereby providing a low health risk, but the minimum vitamin D exceeds ultraviolet exposure thereby providing a health benefit to increased ultraviolet exposure. In response the recommendation to increase ultraviolet exposure is generated. At T4 the personal sensitivity is again decreased. The decrease may be for example, due to the intake of photosensitive medications such as an antibiotic for an infection of the subject person. At T4 the minimum level of vitamin D exceeds the ultraviolet exposure thereby providing a health benefit for increased ultraviolet exposure, but the ultraviolet exposure exceeds the personal sensitivity, thereby providing a health risk to increased ultraviolet exposure. In response the recommendation to decrease ultraviolet exposure is generated. Furthermore, since ultraviolet exposure cannot be increased sufficiently to provide an adequate amount of vitamin D without exceeding the personal sensitivity threshold, the recommendation is shown to include recommending a vitamin D supplement. At T5 the personal sensitivity is increased, perhaps for example due to the subject completing antibiotic treatments. At T5 the personal sensitivity exceeds the ultraviolet exposure, thereby providing a low health risk, but the minimum vitamin D exceeds ultraviolet exposure thereby providing a health benefit to increased ultraviolet exposure. In response the recommendation to increase ultraviolet exposure is generated. At T6 the ultraviolet exposure is significantly increased. The increase may be in response to the recommendation of T5, or based upon a seasonal change in sunlight exposure such as a change from winter to spring, or perhaps the subject person has fully recovered from an illness, or other factor. At T6, the ultraviolet exposure exceeds the minimum level of vitamin D, thereby providing a low health benefit and the ultraviolet exposure significantly exceeds the personal sensitivity, thereby providing a very high health risk, such as sunburn. In response, the recommendation generated is to decrease ultraviolet exposure and an alarm is generated.

The graph of FIG. 6 shows a constant level of minimum vitamin D. In other examples, the minimum level of vitamin D for the purposes of estimating benefits of ultraviolet light may vary depending upon any of a number of factors including the intake of certain vitamin D affecting foods and/or vitamin D supplements by the subject person.

It should be appreciated that while the balanced recommendation is shown by example to recommend increasing, or decreasing, or maintaining levels of ultraviolet exposure, the recommendation can include any number of other recommendations such as changes in diet, sunscreen use, ultraviolet exposure, advice on skin diseases and recommendations to consult medical professionals.

The respective implementations of the present disclosure can be carried out in any appropriate mode, including hardware, software or firmware stored on a storage media and executed computer storage program product, or combination thereof. Alternatively, it is possible to at least partially carry out the implementation of the present disclosure as computer software executed on one or more data processors and/or a digital signal processor. The components and modules or processes of the implementation of the present disclosure can be implemented physically, functionally and logically in any suitable manner. Indeed, the function can be realized in a single member or in a plurality of members, or as a part of other functional members. Thus, it is possible to implement the implementation of the present disclosure in a single member or distribute it physically and functionally between different members and a processor.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations, flow diagrams and/or block diagrams of methods, apparatus (systems) and computer program products according to implementations of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the computer or other programmable data processing apparatus, create means for implementing the functions/acts specified in the blocks of the flowchart illustrations and/or block diagrams.

These computer program instructions may also be stored in a computer readable medium that can direct a computer or other programmable data processing apparatus to function in a particular manner, such that the instructions stored in the computer readable medium produce an article of manufacture including instruction means which implement the functions/acts specified in the blocks of the flowchart illustrations and/or block diagrams.

The computer program instructions may also be loaded onto a computer or other programmable data processing apparatus to cause a series of operational steps to be performed on the computer or other programmable data processing apparatus to produce a computer implemented process such that the instructions which execute on the computer or other programmable apparatus provide processes for implementing the functions/acts specified in the blocks of the flowchart illustrations and/or block diagrams.

The present disclosure is described by use of detailed illustration of the implementations of the present disclosure, and these implementations are provided as examples and do not intend to limit the scope of the present disclosure. Although these implementations are described in the present disclosure, modifications and variations on these implementations will be apparent to those of ordinary skill in the art. Therefore, the above illustration of the exemplary implementations does not confine or restrict the present disclo-

What is claimed is:

1. A method in a computer coupled to a network, the method comprising:
   estimating an ultraviolet light exposure level of a subject person based upon data received from a plurality of sources associated with the subject person, the sources coupled to the network including each of
   at least one social media network-based source, and
   at least one wearable ultraviolet detector;
   mining, using facial recognition technology, the at least one social media network-based source for photographs of the subject person recorded by the plurality of sources, wherein estimating the ultraviolet light exposure level of the subject person is based upon a skin color of the subject person within the photographs;
   estimating a personal sensitivity to ultraviolet light of the subject person based upon personal attributes of the subject person received from at least one database coupled to the computer;
   assessing a health risk of the subject person due to ultraviolet light exposure based upon the ultraviolet light exposure level of the subject person and the personal sensitivity to ultraviolet light of the subject person;
   assessing a health benefit of the subject person due to ultraviolet light exposure based upon the ultraviolet light exposure level of the subject person and the personal sensitivity to ultraviolet light of the subject person;
   generating a balanced ultraviolet light exposure recommendation for the subject person based upon the health risk and the health benefit; and
   rendering the recommendation on an output device coupled to the computer.

2. The method according to claim 1 wherein the generating the balanced ultraviolet light exposure recommendation includes
   recommending an increased exposure to ultraviolet light based upon the health benefit exceeding the health risk, and
   recommending a decreased exposure to ultraviolet light based upon the health risk exceeding the health benefit.

3. The method according to claim 2 wherein
   estimating the personal sensitivity includes estimating an amount of vitamin D corresponding to a good health of the subject person and a level of vitamin D intake associated with the subject person, and
   the assessing the health benefit estimates the level of vitamin D intake to be less than the amount of vitamin D corresponding to the good health, and
   the generating the balanced ultraviolet light exposure recommendation recommends the increased exposure to ultraviolet light based upon the level of vitamin D intake being less than the amount of vitamin D corresponding to the good health.

4. The method according to claim 2 wherein
   the assessing the health risk estimates the ultraviolet light exposure level to exceed the personal sensitivity, and
   the generating the balanced ultraviolet light exposure recommendation recommends the decreased exposure to ultraviolet light based upon the ultraviolet light exposure level being greater than the personal sensitivity.

5. The method according to claim 4 wherein estimating the personal sensitivity to ultraviolet light includes mining a database to determine a medical history of the subject person, wherein the medical history includes an intake of photosensitive medications by the subject person.

6. The method according to claim 4 wherein estimating the personal sensitivity to ultraviolet light includes mining a database to determine a medical history of the subject person and other persons genetically related to the subject person, wherein the medical history includes ultraviolet light exposure related diseases.

7. The method according to claim 4 wherein estimating the personal sensitivity to ultraviolet light includes mining a database to determine personal metadata related to the subject person, wherein the personal metadata includes at least one of a mental state, and an emotional state.

8. The method according to claim 4 wherein estimating the personal sensitivity to ultraviolet light includes mining a database to determine personal diet related to the subject person, wherein the personal diet includes an intake of alcohol by the subject person.

9. The method according to claim 1 wherein the at least one wearable ultraviolet light detector is worn by the subject person and estimating the ultraviolet light exposure level of the subject person includes monitoring the at least one wearable ultraviolet light detector.

10. The method according to claim 1 wherein
    one of the plurality of sources includes a wearable location detection device worn by the subject person and
    estimating the ultraviolet light exposure level of the subject person includes determining a time and location of the subject person and mining a database for an ultraviolet light exposure map and estimating the ultraviolet light exposure level based upon the time and location of the subject person and the ultraviolet light exposure map.

11. The method according to claim 1 wherein estimating the personal sensitivity to ultraviolet light of the subject person includes estimating an amount of time sunscreen is worn while the subject person is being exposed to ultraviolet light based upon at least one of purchases by the subject person, by mining the social media network-based resource for comments indicative of the use of sunscreen by the subject person, and images indicative of the use of sunscreen by the subject person.

12. A computer device coupled to a network, the computer device comprising:
    an ultraviolet light exposure estimator adapted to estimating an ultraviolet light exposure level of a subject person based upon data received from a plurality of sources associated with the subject person, the sources the sources coupled to the network including each of
    at least one social media network-based source, and
    at least one wearable ultraviolet detector;
    mining, using facial recognition technology, the at least one social media network-based source for photographs of the subject person recorded by the plurality of sources, wherein estimating the ultraviolet light exposure level of the subject person is based upon a skin color of the subject person within the photographs;
    a personal sensitivity to ultraviolet light estimator adapted to estimate a personal sensitivity to ultraviolet light of the subject person based upon personal attributes of the subject person received from at least one database coupled to the computer device;
    a health risk assessor adapted to assess a health risk of the subject person due to ultraviolet light exposure based upon the ultraviolet light exposure level of the subject person and the personal sensitivity to ultraviolet light of the subject person;

a health benefit assessor adapted to assess a health benefit of the subject person due to ultraviolet light exposure based upon the ultraviolet light exposure level of the subject person and the personal sensitivity to ultraviolet light of the subject person;

a balanced ultraviolet light exposure recommender adapted to generate a balanced ultraviolet light exposure recommendation for the subject person based upon the health risk and the health benefit including recommending an increased exposure to ultraviolet light based upon the health benefit exceeding the health risk, and recommending a decreased exposure to ultraviolet light based upon the health risk exceeding the health benefit; and an output device adapted to render the recommendation.

13. The computer device according to claim 12 wherein
the personal sensitivity to ultraviolet light estimator estimates an amount of vitamin D corresponding to a good health of the subject person and a level of vitamin D intake associated with the subject person, and
the health benefit assessor estimates the level of vitamin D intake to be less than the amount of vitamin D corresponding to the good health, and
the balanced ultraviolet light exposure recommender recommends the increased exposure to ultraviolet light based upon the level of vitamin D intake being less than the amount of vitamin D corresponding to the good health.

14. The computer device according to claim 12 wherein
the health risk assessor estimates the ultraviolet light exposure level to exceed the personal sensitivity, and
the balanced ultraviolet light exposure recommender recommends a decreased exposure to ultraviolet light based upon the ultraviolet light exposure level being greater than the personal sensitivity.

15. The computer device according to claim 12 wherein
one of the plurality of sources includes a wearable location detection device worn by the subject person adapted to determine a time and location of the subject person and
the ultraviolet light exposure estimator receives an ultraviolet light exposure map and estimates the ultraviolet light exposure level based upon the time and location of the subject person and the ultraviolet light exposure map.

16. A computer storage program product comprising:
a storage medium readable by a processing circuit and storing instructions for execution by the processing circuit configured to perform a method comprising:

estimating an ultraviolet light exposure level of a subject person based upon data received from a plurality of sources associated with the subject person, the sources coupled to the network including each of including each of
at least one social media network-based source, and
at least one wearable ultraviolet detector;
mining, using facial recognition technology, the at least one social media network-based source for photographs of the subject person recorded by the plurality of sources, wherein estimating the ultraviolet light exposure level of the subject person is based upon a skin color of the subject person within the photographs;
estimating a personal sensitivity to ultraviolet light of the subject person based upon personal attributes of the subject person received from at least one database;
assessing a health risk of the subject person due to ultraviolet light exposure based upon the ultraviolet light exposure level of the subject person and the personal sensitivity to ultraviolet light of the subject person;
assessing a health benefit of the subject person due to ultraviolet light exposure based upon the ultraviolet light exposure level of the subject person and the personal sensitivity to ultraviolet light of the subject person; and
generating a balanced ultraviolet light exposure recommendation for the subject person based upon the health risk and the health benefit.

17. The computer storage program product according to claim 16 wherein
the generating the balanced ultraviolet light exposure recommendation includes recommending an increased exposure to ultraviolet light based upon the health benefit exceeding the health risk, and recommending a decreased exposure to ultraviolet light based upon the health risk exceeding the health benefit,
the assessing the health risk estimates the ultraviolet light exposure level to exceed the personal sensitivity, and
the generating the balanced ultraviolet light exposure recommendation recommends a decreased exposure to ultraviolet light based upon the ultraviolet light exposure level being greater than the personal sensitivity.

18. The computer storage program product according to claim 17 wherein estimating the personal sensitivity to ultraviolet light includes mining a database to determine personal metadata related to the subject person, wherein the personal metadata includes at least one of a mental state, and an emotional state.

\* \* \* \* \*